United States Patent [19]

Kullenberg

[11] Patent Number: 5,084,269

[45] Date of Patent: Jan. 28, 1992

[54] ADJUVANT FOR DOSE TREATMENT WITH ANTIGENS

[76] Inventor: Fred W. Kullenberg, Ginger Woods Rd., Lot 20, Valley, Nebr. 68064

[21] Appl. No.: 312,675

[22] Filed: Feb. 16, 1989

Related U.S. Application Data

[63] Continuation-in-part of Ser. No. 927,392, Nov. 6, 1986, abandoned.

[51] Int. Cl.$^5$ ............. A61K 39/00; A61K 39/39
[52] U.S. Cl. ............................. 424/88; 424/89; 424/92; 424/93
[58] Field of Search ................ 424/88, 89, 92, 93

[56] References Cited

U.S. PATENT DOCUMENTS

| | | | |
|---|---|---|---|
| 3,752,886 | 8/1973 | Munder et al. | 424/199 |
| 4,053,585 | 10/1977 | Allison et al. | 424/92 |
| 4,117,113 | 9/1978 | Allison et al. | 424/89 |
| 4,323,563 | 4/1982 | Takami et al. | 424/199 |
| 4,425,330 | 1/1984 | Norcross et al. | 424/92 |
| 4,591,499 | 5/1986 | Linn et al. | 424/93 |

OTHER PUBLICATIONS

Reynolds, J. A., et al., "Infection and Immunity", Jun. 1980, pp. 937–943.
Nervig et al., "Advances in Carriers and Adjuvants for Veterinary Biologics", (1984), pp. 3–9, 11–23, 51–59, 105–113, 115–119.
Jolles and Paraf, "Chemical and Biological Basis of Adjuvants", (1973), pp. 108–110.
Burgh et al., "Comparison of Inactivated Newcastle Disease Viral Vaccines Containing Different Emulsion Adjuvants", Am. J. Vet. Res., vol. 44, No. 1, pp. 72–75, (1983).
Braugh et al., "Comparison of Inactivated Newcastle Disease Viral Vaccines Containing Different Emulsion Adjuvants", Am. J. Vet. Res., 44:72–75, Jan. 1983.
Reynolds et al., "Adjuvant Activity of a Novel Metabolizable Lipid Emulsion with Inactivated Viral Vaccines", Infect. Immun., 28:937–943, Jun. 1980.

Primary Examiner—John Doll
Assistant Examiner—Robert D. Budens
Attorney, Agent, or Firm—Zarley, McKee, Thomte, Voorhees & Sease

[57] ABSTRACT

Therapeutic effectiveness of antigen doses is improved by an adjuvant comprised of a mixture of lecithin in combination with a carrier which may be selected from the group consisting of non-edible oils such as mineral oil and edible triglyceride oils such as soybean oil.

7 Claims, No Drawings

ADJUVANT FOR DOSE TREATMENT WITH ANTIGENS

CROSS REFERENCE TO RELATED APPLICATION

This application is a continuation-in-part of Ser. No. 927,392 filed Nov. 6, 1986, now abandoned.

BACKGROUND OF THE INVENTION

From time to time in the past there have been many efforts at the development of antigens for use in therapeutic treatments for the immunization of animals of the mammalian and avian orders. These antigens develop an immune response within the animal that may effectively function therapeutically with regard to certain disease disorders. For example, U.S. Pat. No. 3,479,430 deals with immunizing porcine animals against transmissible gastroenteritis by injecting into the pregnant sow before farrowing a vaccine of attenuated transmittible gastroenteritis virus. Other antigen type products have been developed for canine corona vaccine, for porcine atrophic rhinitis, and for porcine rotavirus.

The ability of these antigen based medicinals to properly develop the desired immune response in the animal is in part based upon the effect of the adjuvant employed with the vaccine. Put another way, the precise means by which the antigen is presented can either distract from the activity, or enhance the activity, in terms of developing the desired immune response.

In the past there have been many adjuvants used, see for example Reynolds et al., "Adjuvant Activity of a Novel Metabolizable Lipid Emulsion with Inactivated Viral Vaccines,"*Infection and Immunity*, June 1980 pp. 397–943, which discusses such adjuvants as glycerine, glycerine in combination with lecithin, Freund adjuvant, and others.

The use of adjuvants in combination with antigens is not a new or unique method of enhancing immunization in animals. In 1926, Glenny, et al. reported that the addition of potassium alum to diptheria toxoid resulted in the formation of a precipitate that bound the toxoid, Glenny, A.T., et al., *Toxoid Precipitated with Alum.*, J. Path. Bacteriol. 34:267–75, 1931. The precipitate, when resuspended in water was shown to be enhanced in its ability to produce immunity over the original toxoid from which it was produced.

Further, the use of oil-based adjuvants is not new or unique. Such use appeared in the literature as early as 1916 when Le Moignac and Pinoy of France emulsified a suspension of Salmonella typhimurium in liquid paraffin (mineral oil) by using lanolin as an emulsifier and obtained an improved immune response in injected animals.

Other reports of various oil combinations incorporated as adjuvants appeared in the literature between 1935 and 1943, McKercher, et al., *A review of the current status of oil adjuvants in foot-and-mouth disease vaccines*, Dev. Biol. Stand. 35:107–12, 1977. These included the use of oil adjuvants in vaccines for bovine pleuropneumonia, brucellosis and anthrax of cattles.

In the early 1900's Freund combined paraffin (mineral oil) with whole killed tubercle bacilli as an adjuvant (Freund's Complete Adjuvant or FCA) for enhancing the immunologic response in various experimental animals with considerable success. This led to later studies using an extract of the tubercle bacillus, instead of whole bacteria, combined with the oil adjuvant. The term Freund's Incomplete Adjuvant (FIA) came from these later studies and is commonly used today. While effective as adjuvants when combined with a variety of antigens, unfortunately, both FCA and FIA which are oil-based adjuvants, are much too irritating for routine use as adjuvants in commercially produced biological products for use in the mammalian and avian species of animals.

In 1979, Munder, P.G. et al., reported on the immunomodulating and other biological effects of the phospholipid, lysophosphatidylcholine (Lysolecithin). The report dealt primarily with the ability of Lysolecithin, as a surface active agent, to alter cell membranes in such a way as to facilitate cell interactions, activate synthesis of regulatory molecules, or even function as analogs of naturally occurring regulatory molecules, Nervig, R.M., *Advances in Carriers and Adjuvants for Veterinary Biologics*, Iowa State University Press, p. 17, 1986. Its potential role as an "antigen presenter" was not addressed.

It is a primary object of the present invention to provide an improved adjuvant which can be used for the immunization of animals of the mammalian and avian orders for administration of antigens in an manner which substantially improves the antigen from the standpoint of reducing the amount of irritation, and from the standpoint of enhancing the effectiveness of the desired immunization response.

The method of accomplishing the above primary objective as well as others will become apparent from the detailed description of the invention which will follow hereinafter.

SUMMARY OF THE INVENTION

Improved mammalian animal and avian antigen systems which comprise a small but effective amount of an antigen capable of providing a desired immune response, and in combination therewith an adjuvant comprised of lecithin in combination with a carrier which itself can be selected from the group consisting of edible and non-edible oils.

DETAILED DESCRIPTION OF THE INVENTION

The ability to induce an immune response depends on the chemical and molecular complexity of the inducing agent, the immune response characteristics of the host organism, and the form by which the introducing agent is administered. The chemical inducing agent, that is the antigen, portion of the compositions of this invention is not critical and can be any one of a wide variety of antigens capable of producing a desired immune response in the host organism. Typical antigens which may be used are modified live or attenuated bacteria and viruses, inactivated or killed bacteria and viruses and the like or other agents of suitable molecular structure to act as antigens. Some examples of those suitable, without any indication that they are necessarily limiting are transmissible gastroenteritis virus, corona-virus, parvo virus, errota virus, atrophic rhinitis inducing virus, the bacterial pathogen Haemophilus Pleuropnemonia, canine coronavirus, feline coronavirus, and other antiviral vaccination antigens capable of producing a desired and specific immunological response.

As earlier mentioned, the vaccines may be viral products or bacterial products. Suitable bacterial products may include the following:

| Large animal | Small animal | Poultry |
| --- | --- | --- |
| Bacterial Products | Bacterial products | Bacterial products |
| Clostridium | None | Haemophilus |
| Pasteurella | | Erysipelothrix |
| Bordetella | | |
| Erysipelothrix | | |
| Escherichia | Viral products | Viral products |
| Salmonella | Rabies | None |
| Haemophilus | | |
| Campylobacter | | |
| Staphylococcus | | |
| Moraxella | | |
| Streptococcus | | |
| Viral products | | |
| Rabies | | |
| Parvovirus | | |
| Others, previously mentioned | | |

It is understood that the term "biologic" as used here is therefore broad enough to include antigens producing an immune response which may include both viral products and bacterial products or other agents of suitable molecular structure to act as antigens.

In addition to the desired active, that is the portion of the veterinary biologic composition which produces the immune response, such as those previously presented, the antigen must also be presented in a suitable adjuvant for delivery in dose form as a veterinary biologic.

It has now been discovered that the adjuvant of this invention has significant advantages in that it decreases the irritation response in the host, while simultaneously providing for increased effectiveness because of increased immune response within the host organism.

In the composition of the present invention, the biologic itself is present in an amount sufficient to provide the desired immune response. As those skilled in the art know, the amount of active will vary considerably depending upon the precise active employed, the animals to which the biologic is to be administered, the nature of the antigen, and the level of desired antibody sought in the host. Generally where the antigen is a bacteria, whether living or dead, the titer should be from $10^3$ to $10^9$, preferably from $10^5$ to $10^8$ organisms per dose. Where the antigen is a virus, the titer per dose should be from $10^2$ to $10^8$ TCID$_{50}$'s (Tissue Culture Infective Doses), preferably from $10^4$ to $10^6$ TCID$_{50}$'s, either as a pre-inactivation titer or actual live virus content of the biologic.

As earlier mentioned, the biologic composition comprises the antigen in an amount sufficient to produce the desired immunological response, coupled with the non-toxic pharmaceutically acceptable adjuvant combination of this invention. The adjuvant combination comprises, based on the weight of the total adjuvant composition, from about 0.5% by weight to about 30% by weight of lecithin, preferably from about 5.0% by weight to about 10% by weight of lecithin, with the lecithin itself being combined with a carrier, which may be an edible or non-edible oil. If an oil, the oil comprises from about 70% by weight of the adjuvant composition to about 95.5% by weight of the adjuvant composition, preferably from about 90% by weight to about 95% by weight of the adjuvant composition.

Unexpectedly, it has been found that when the adjuvant composition is comprised of lecithin in combination with an oil, as described above, and the biologic is thereafter administered, for example, either subcutaneously or parenterally or orally, as the case may be, there is a decrease in irritation within the host animal, and the adjuvant simultaneously induces increased systemic immunity.

The lecithin component of the adjuvant may be obtained from several sources. Lecithin generally refers to a complex naturally occurring mixture of phosphatides and trigly-cerides obtained by water-washing crude vegetable oils and separating and drying the resulting hydrated gums. Crude soybean lecithin obtained by this procedure contains approximately 62-64% acetone insoluble phosphatides. In commercial usage, the term is also applied to refined, modified or fractionated products such as the aceton-insoluble phospholipids and glycolipids remaining after removal of the triglycerides and vegetable oil by acetone washing. Such factionated, de-oiled lecithins contain up to 99% AI (acetone insolubles).

The AI content is one of the basic specifications utilized to classify the wide variety of commercial lecithins available. In older literature, and to some extent today, particularly in the medical fields as opposed to the foods industry, the term lecithin has been used to refer to a single phospholipid, the choline ester of phosphatidic acid, called phosphatidylcholine. In addition to phosphatidylcholine, fractionated, de-oiled soy lecithins contain phosphatidylethanolamine, phosphatidylinositol, phosphatidylserine, phosphatidic acids and smaller amounts of minor phosphatides, and significant amounts of glycolipids.

As appreciated, lecithin is a commercially available material which may be obtained from a variety of sources, for example Central Soya, Chemurgy Division, Fort Wayne, Indiana. For further details with regard to lecithin, its precise composition and its processing preparation and isolation techniques from, for example, soybeans see a brochure of Central Roya Co., Inc., copyright 1985, entitled "lec-i-thin," available from Central Soya, Chemurgy Division, 1300 Fort Wayne National Bank Building, P.O. Box 1400, Fort Wayne, Indiana 46801-1400. The suitable lecithin, as previously described is mixed within the prescribed ranges with a carrier which may be either a paraffin oil such as mineral oil and therefore not edible, or an edible oil such as triglyceride oil. When the carrier is an oil, suitable triglyceride edible oils include cotton seed oil, soybean oil, coconut oil, rapeseed oil, peanut oil, olive oil, palm oil, palm kernel oil, sunflower seed oil, wallflower oil, pilchard oil, and the like. Preferred paraffin oils are mineral oils such as mineral oil, Light, U.S. pharmaceutical grade.

The compositions of the inventions are solutions and may be prepared using several methods, depending on the lecithin/carrier ratio desired. For lecithin/oil ratios up to 40:60, the solutions may be prepared by heating the oil to 40° C. to 60° C. and slowly adding the desired amount of lecithin using gentle agitation until thoroughly dissolved. For lecithin/oil ratios in excess of 40:60 up to and including ratios of 77:23 water, acetone or a combination of both must be used as solvents in addition to heating. For Lecithin/carrier combinations wherein an aqueous carrier is utilized, other suitable solubilization methods can be employed.

The following are especially preferred compositions for use in the invention:
Fractionated, De-oiled Lecithin - 5-30% w/v
Light Mineral (Drakeol 6 VR) - 60-90% v/v
or Fractionated, De-oiled Lecithin - 5-30% w/v
Refined Soybean Oil - 60-90% v/v The preferred chemical profile for Acetone fractionated, de-oiled lecithin in the compositions above is as follows:

| MAJOR PHOSPHOLIPIDS | |
|---|---|
| Phosphatidylcholine | 23% |
| Phosphatidylethanolamine | 20% |
| Phosphatidylinositol | 14% |
| Phosphatidic Acid | 5-8% |
| MINOR PHOSPHOLIPIDS | |
| Phosphatidylserine | 2% |
| Others* | 7-8% |
| | 71-75% |
| *Includes: Acylphosphatidylethanolamine | |
| Diphosphatidylethanolamine | |
| Lysophosphatidylethanolamine | |
| Lysophosphatidylcholine | |
| Unidentified Phospholipids | |
| GLYCOLIPIDS | |
| Esterified Steryl Glucosides | 6% |
| Steryl Glucosides and Cerebrosides | 3-4% |
| Digalactosyl Diglycerides | 1.5-2% |
| Unidentified Glycolipids | 3-4% |
| | 13-16% |
| NEUTRAL LIPIDS | |
| Triglycerides | 2-3% |
| Free Fatty Acids | 0-1% |
| Campesterol, Stigmasterol and B-Sitosterol | 0.1-0.2% |
| Others** | 0.2% |
| | 2.3-4.2% |
| **Includes: Diglycerides | |
| Monoglycerides | |
| Sterol Esters | |
| Pigments | |
| Tocopherols | |
| Others | |
| SUGARS | |
| Sucrose | 3.5% |
| Raffinose | 0.5% |
| Stachyose | 4.0% |
| | 8.0% |
| MOISTURE | 0.5-1.0% |
| In summary, the AI composition is basically: | |
| Major Phospholipids | 60% |
| Minor Phospholipids | 10% |
| Glycolipids | 22% |
| Sugars | 8% |

The adjuvant can be used at varying levels in different biologics. The amount of adjuvant in each product will be determined by individual testing with each antigen. Ordinarily, an adjuvant in a vaccine must comprise 30% to 50% of the resulting composition. However, it has been found that the adjuvant of the present invention is sufficiently efficacious that it may comprise as little as 5% of the composition and achieve desired results.

The following working example will demonstrate that the compositions of the invention do in fact enhance immune responses.

EXAMPLE

A group of 10 three month old pigs was divided into two groups of four pigs and one group of two pigs. All pigs were bled prior to injection and determined to be sero-negative (no antibody titer) to the bacterial pathogen, Haemophilus pleuropneumonia.

A 2 ml. dose of Haemophilus bacterin, containing killed Haemophilus organisms (sterotype 5) and containing either 30% of an adjuvant of the invention which itself was 10% by weight of fractionated de-oiled lecithin and 90% by weight of light mineral oil (Drakol 6 VR) or 20% Aluminum Hydroxide Gel as an adjuvant was injected, respectively, into a group of four pigs. Two pigs were not inoculated to serve as contact controls. A second inoculation of the same dosage and type of bacterin was administered 28 days after the first inoculation, and the animals bled two weeks later, to determine the level of antibody produced by the inoculations. The results were as follows:

| | Average Titers | |
|---|---|---|
| | Pre-Test | 28 Days Post |
| Adjuvant of the invention (4 pigs) | 0 | 1:16 |
| Aluminum Hydroxide Group (4 pigs) | 0 | 1:2 |
| Contact Controls (2 pigs) | 0 | 0 |

In this test, the adjuvant of the invention produces an 8 fold increase in antibody titer against *H. pleuropneumonia* (serotype 5) organisms.

Similar results are obtained in that the level of antibody produced during inoculation is significantly increased, with a decrease in irritation for other biologics, including bacterial based biologics and virus based biologics.

The reasons why the improvement enhances the immune response and reduces irritation are not known for certain, and therefore, applicant prefers not be bound to any specific theory or explanation.

The following are some possible mechanisms that could function alone or in combinations to affect the enhanced immune response:

(1) Lecithins have high levels of Phospholipids and Glycolipids, natural animal cell components found in high levels in all cell membrane, which may offer unique antigen binding stereochemistry that improves the antigen presentation to the immune system by:

(a) Improving antigen transport by macrophages and lymphocytes.

(b) The amphoteric Glycolipids have simple and complex sugar residues that act as specifically sensitive antigen binding sites.

(c) Selected other minor phosphatides such as the Lysolecithins might provide unique amphipathic properties or polar stereo-chemistries that enhance antigen presentation.

(2) The lipophilic regions of the Phospholipid and Glycolipid molecules allow emulsification of the oil phase in the finished biological in such a way that the presentation of the oil in body creates an ideal depot situation without unacceptable irritation.

It therefore can be seen that the invention accomplishes its stated objectives as well as others.

What is claimed is:

1. A biologic for use in the mammalian and avian orders of animals which includes a small but effective amount of immune response producing antigen in combination with an adjuvant which is from 5.0% by weight to 10% by weight of lecithin, and from 90% by weight to 95% by weight of an oil carrier.

2. The biologic of claim 1 wherein the oil carrier is a mineral oil.

3. The biologic of claim 1 wherein the oil carrier is an edible oil.

4. The biologic of claim 1 wherein the edible oil is a triglyceride oil.

5. The biologic of claim 1 wherein the biologic contains as an antigen a bacteria.

6. The biologic of claim 1 wherein said biologic contains as an antigen a virus.

7. A method of producing an effective immune response in animals, which includes treating the animal with a biologic containing a small but effective amount of immune response producing antigen, said method comprising:

producing a biologic by combining said antigen with an adjuvant which is from 5% by weight to 10% by weight of lecithin, and from 90% by weight to 95% by weight of an oil carrier; and thereafter treating said animal with said biologic.

* * * * *